United States Patent
Hassan et al.

(10) Patent No.: US 10,513,652 B2
(45) Date of Patent: Dec. 24, 2019

(54) ADDITION OF MONOVALENT SALTS FOR IMPROVED VISCOSITY OF POLYMER SOLUTIONS USED IN OIL RECOVERY APPLICATIONS

(71) Applicant: Saudi Arabian Oil Company, Dhahran (SA)

(72) Inventors: Saleh F. Hassan, Khobar (SA); Abdulkareem M. AlSofi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/660,420

(22) Filed: Jul. 26, 2017

(65) Prior Publication Data
US 2018/0030185 A1    Feb. 1, 2018

Related U.S. Application Data

(60) Provisional application No. 62/366,926, filed on Jul. 26, 2016.

(51) Int. Cl.
*C09K 8/588* (2006.01)
*C08F 220/56* (2006.01)
(Continued)

(52) U.S. Cl.
CPC ............ *C09K 8/588* (2013.01); *C08F 220/56* (2013.01); *C09K 8/57* (2013.01); *G01N 11/00* (2013.01)

(58) Field of Classification Search
None
See application file for complete search history.

(56) References Cited

U.S. PATENT DOCUMENTS 3,572,354 A    3/1971   Tinsley et al.
3,584,686 A *  6/1971   Fulford ................. C09K 8/528
                                                       166/275

(Continued)

FOREIGN PATENT DOCUMENTS

CA    1136839 A    12/1982
DE    4330689 C2   5/1996
(Continued)

OTHER PUBLICATIONS

International Search Report and Written Opinion for International Application No. PCT/US2017/043863; International Filing Date Jul. 26, 2017; dated Oct. 19, 2017 (pp. 1-17).

(Continued)

*Primary Examiner* — Andrew Sue-Ako
(74) *Attorney, Agent, or Firm* — Bracewell LLP; Constance G. Rhebergen; Brian H. Tompkins

(57) ABSTRACT

An oil recovery composition having a brine, a hydrolyzable polymer, and a monovalent cations to divalent cations ration in the range of about 3:1 to about 4.5:1 is provided. An oil recovery composition may be formed from a brine recovered from production water and a polymer. A monovalent salt may be added to the brine recovered from production water to form a modified brine and achieve a modified monovalent cations to divalent cations ratio in the range of about 3:1 to about 4.5:1. Processes for forming the oil recovery composition and enhanced oil recovery using the oil recovery composition are provided.

8 Claims, 2 Drawing Sheets

(51) Int. Cl.
*C09K 8/57* (2006.01)
*G01N 11/00* (2006.01)

(56) References Cited

U.S. PATENT DOCUMENTS

| | | | |
|---|---|---|---|
| 3,827,499 A | | 8/1974 | Norton et al. |
| 3,908,764 A | | 9/1975 | Harvey |
| 4,395,340 A | * | 7/1983 | McLaughlin .............. C08F 2/10 |
| | | | 166/266 |
| 4,467,869 A | | 8/1984 | Gupta |
| 4,582,137 A | * | 4/1986 | Schmitt .................. C09K 8/584 |
| | | | 166/270.1 |
| 4,702,319 A | | 10/1987 | Bock et al. |
| 4,709,759 A | | 12/1987 | Bock et al. |
| 5,073,270 A | * | 12/1991 | Gallup ...................... C02F 1/70 |
| | | | 166/300 |
| 5,612,293 A | | 3/1997 | Swartwout et al. |
| 6,669,752 B2 | | 12/2003 | Arnold et al. |
| 8,327,935 B2 | | 12/2012 | Crill |
| 8,789,594 B2 | | 7/2014 | Curole et al. |
| 2012/0199355 A1 | | 8/2012 | Boluk et al. |
| 2015/0107840 A1 | * | 4/2015 | Ligthelm .............. E21B 43/162 |
| | | | 166/305.1 |
| 2016/0122622 A1 | | 5/2016 | Dwarakanath et al. |
| 2016/0122623 A1 | | 5/2016 | Dwarakanath et al. |
| 2016/0122624 A1 | | 5/2016 | Dwarakanath et al. |
| 2016/0122626 A1 | | 5/2016 | Dwarakanath et al. |

FOREIGN PATENT DOCUMENTS

| | | |
|---|---|---|
| GB | 2028893 A | 3/1980 |
| WO | 9619544 A3 | 2/1997 |
| WO | 2014113445 A1 | 7/2014 |

OTHER PUBLICATIONS

Algharaib, et al.; "Enhancing Recovery in High Salinity Oil Reservoirs through Optimized Polymer Flood." IPTC 14685, International Petroleum Technology Conference Feb. 7-9, 2012; 17 pages.

Algharaib, M., et al.; "Investigation of polymer flood performance in high salinity oil reservoirs." SPE 149133, SPE/DGS Saudi Arabia Section Technical Symposium and Exhibition May 15-18, 2011; pp. 1-8.

Henthorne, Lisa, et al. "Impact of Water Softening on Chemical Enhanced Oil Recovery Project Economics." SPE 169165-MS, SPE Improved Oil Recovery Symposium Apr. 12-16, 2014; pp. 1-12.

Lange, Werner, et al.; "Recent Results on the Use of Polymers in Tertiary Oil Recovery in Brines of High Salinity." SPE 8983, SPE 5th International Symposium on Oilfield and Geothermal Chemistry Symposium May 28-30, 1980; pp. 87-94.

Martin, et al.; "The Effect of Hyrolysis of Polyacrylamide on Solution viscosity, Polymer Retention and Flow Resistance Properties." SPE 5339, SPE Rocky Mountain Regional Meeting, Apr. 7-9, 1975; pp. 1-8.

Nashawi, Ibrahim S. "Laboratory Investigation of the Effect of Brine Composition on Plymer Solutions—Part 1: Partially Hydrolyzed Polyacrylamide (HPAM) Case." SPE 23533, Society of Petroleum Engineers (1991). pp. 1-23.

Seright, Randall S., et al. "Stability of Partially Hydrolyzed Polyacrylamides at Elevated Temperatures in the Absence of Divalent Cations." SPE 121460, SPE International Symposium on Oilfield Chemistry, Apr. 20-22, 2009; 15 pages.

Sohn, Wolfgang O., et al.; "Preconditioning Concepts in Polymer Flooding in High-Salinity Reservoirs: Laboratory Investigations and Case Histories." SPE 17675, SPE Reservoir Engineering, Nov. 1990; pp. 503-507.

Vermolen, Esther CM, et al. "Low-salinity polymer flooding: improving polymer flooding technical feasibility and economics by using low-salinity make-up brine." IPTC 17342, IPTC 2014: International Petroleum Technology Conference. 2014. pp. 1-15.

Ward, J. S., et al.; "Prediction of Viscosity for Partially Hydrolyzed Polyacrylamide Solutions in the Presence of Calcium and Magnesium Ions." SPE 8978, Society of Petroleum Engineers Journal, Oct. 1981; pp. 623-631.

Zaitoun, et al. "Limiting Conditions for the Use of Hydrolyzed Polyacrylamides in Brines Containing Divalent Ions." SPE 11785, SPE Oilfield and Geothermal Chemistry Symposium. Society of Petroleum Engineers, (1983) pp. 143-150.

\* cited by examiner

ADDITION OF MONOVALENT SALTS FOR IMPROVED VISCOSITY OF POLYMER SOLUTIONS USED IN OIL RECOVERY APPLICATIONS

CROSS-REFERENCE TO RELATED APPLICATIONS

This application claims priority from U.S. Provisional Application No. 62/366,926 filed Jul. 26, 2016, and titled "ADDITION OF MONOVALENT SALTS FOR IMPROVED VISCOSITY OF POLYMER SOLUTIONS USED IN OIL RECOVERY APPLICATIONS." For purposes of United States patent practice, this application incorporates the contents of the Provisional Application by reference in its entirety.

BACKGROUND

Field of the Disclosure

Embodiments of the disclosure generally relate to an oil recovery process and enhancing oil recovery from a reservoir formation. In particular, embodiments of the disclosure relate to an oil recovery process using a polymer.

Description of the Related Art

The use of improved oil recovery (also referred to as enhanced oil recovery (EOR)) processes has greatly benefited the oil and gas industry by increasing the production of hydrocarbon bearing wells and fields. The EOR processes used in modern oil and gas operations may include chemical, gas, thermal, and microbial based processes. Water injection (alternatively referred to as water flooding) has been widely used to maintain reservoir pressures and displace hydrocarbon toward wells, thus increasing the production of liquid hydrocarbons in subterranean reservoir. Chemical EOR applications are water-based and use chemicals such as polymers, surfactants, alkalines, or combinations thereof dissolved in water and co-injected. The water source may be derived from freshwater, (for example, aquifers or surface water), saltwater/brackish sources on the surface (for example, river/sea water mixtures), or in water reservoirs (for example, aquifer water or brines coproduced from oilfield reservoirs).

SUMMARY

Water flooding, including the injection of water into a reservoir formation, may be used in EOR processes. Some EOR techniques add a polymer to the water to increase the viscosity of injected water to achieve more favorable mobility and counteract heterogeneity effects. Depending on the source water and its composition, more resistant polymers, higher concentrations of polymers, or both may be used to form an EOR solution having a desired viscosity. However, the use of such polymers at the relatively high concentrations needed to achieve a desired viscosity may increase operating costs of EOR operations and consume large quantities of the polymer. The salinities and hardness of the water used in such EOR operations may result in lower viscosities of polymer solutions and may require the use of more resistant polymers and relatively high concentration of polymers. As an alternative, water softening facilities may be used to enable the use of less resistant polymer or lower concentrations of polymer, but the use of such facilities may increase the capital cost of EOR operations.

In some embodiments, a composition for enhancing oil recovery in a hydrocarbon reservoir formation is provided. The composition includes a modified brine having a modified monovalent cations to divalent cations ratio in a range of 3:1 to 4.5:1 and a hydrolyzable polymer having a concentration of 0.05 weight (wt) % to 0.5 wt %. The monovalent cations to divalent cations ratio is selected to achieve a target viscosity of the composition, and the modified brine formed by adding a monovalent salt to a brine to modify the ratio of monovalent cations to divalent cations of the brine. In some embodiments, the hydrolyzable polymer includes polyacrylamide. In some embodiments, the monovalent cations include sodium cations. In some embodiments, the divalent cations include at least of calcium cations and magnesium cations. In some embodiments, the target viscosity is at least 4 centipoise at conditions of the hydrocarbon reservoir formation. In some embodiments, the brine includes brine recovered from production water. In some embodiments, the brine includes treated seawater or untreated seawater. In some embodiments, the brine includes aquifer water. In some embodiments, the monovalent salt includes sodium chloride (NaCl). In some embodiments, the composition includes a surfactant.

In some embodiments, a method of enhancing oil recovery in a hydrocarbon reservoir formation is provided. The method includes introducing an oil recovery composition into the reservoir formation. The oil recovery composition includes a modified brine having a modified monovalent cations to divalent cations ratio in a range of 3:1 to 4.5:1 and a hydrolyzable polymer having a concentration of 0.05 weight (wt) % to 0.5 wt %. The monovalent cations to divalent cations ratio is selected to achieve a target viscosity of the composition, and the modified brine formed by adding a monovalent salt to a brine to modify the ratio of monovalent cations to divalent cations of the brine. In some embodiments, the hydrolyzable polymer includes polyacrylamide. In some embodiments, the monovalent cations include sodium cations. In some embodiments, the divalent cations include at least of calcium cations and magnesium cations. In some embodiments, the target viscosity is at least 4 centipoise at conditions of the hydrocarbon reservoir formation. In some embodiments, the method includes preparing the oil recovery composition before introducing the oil recovery composition into the reservoir formation. The preparing includes recovering the brine from production water, adding the monovalent salt to the brine to form the modified brine, and adding the hydrolyzable polymer to the brine. In some embodiments, the brine includes treated seawater or untreated seawater. In some embodiments, the brine includes aquifer water. In some embodiments, the oil recovery composition includes a surfactant.

In some embodiments, a method of forming a composition having a target viscosity for enhancing oil recovery in a hydrocarbon reservoir formation is provided. The method includes determining a ratio of monovalent cations to divalent cations of a brine and adding a monovalent salt to the brine to modify the ratio of monovalent cations to divalent cations of the brine to a range of 3:1 to 4.5:1. The method also includes adding a hydrolyzable polymer to the brine to form the composition having the target viscosity, wherein the hydrolyzable polymer has a concentration of 0.05 weight (wt) % to 0.5 wt %. In some embodiments, the method includes recovering the brine from a production water. In some embodiments, the brine includes treated seawater or untreated seawater. In some embodiments, the brine includes aquifer water. In some embodiments, the method includes adding a surfactant to the bring to form the composition. In some embodiments, hydrolyzable polymer includes polyacrylamide. In some embodiments, the monovalent cations include sodium cations. In some embodiments, the divalent cations include at least of calcium cations and magnesium cations. In some embodiments, the target viscosity is at least 4 centipoise at conditions of the hydrocarbon reservoir formation. In some embodiments, adding a monovalent salt to the brine includes mixing the monovalent salt and the brine for a mixing time period. In some embodiments, the monovalent salt includes NaCl.

BRIEF DESCRIPTION OF THE DRAWINGS

These and other features, aspects, and advantages of the present disclosure will become better understood with regard to the following descriptions, claims, and accompanying drawings. It is to be noted, however, that the drawings illustrate only several embodiments of the disclosure and are therefore not to be considered limiting of the disclosure's scope as it can admit to other equally effective embodiments.

DETAILED DESCRIPTION

The present disclosure will now be described more fully with reference to the accompanying drawings, which illustrate embodiments of the disclosure. This disclosure may, however, be embodied in many different forms and should not be construed as limited to the illustrated embodiments set forth in the disclosure. Rather, these embodiments are provided so that this disclosure will be thorough and complete, and will fully convey the scope of the disclosure to those skilled in the art.

Salts in the source brine used to form the polymer solution may have adverse effects on polymer viscosity. Such salts may neutralize electrical charges along the polymer, enabling the polymer chain to coil into a tightly wound sphere and reducing the surface exposed to the solvent. This activity decreases interactions between the polymer particles dissolved in the brine, decreases repulsion between the polymer particles, and decreases the viscosity of the hydrolyzed polymer solution. Divalent salts may have a greater effect on polymer viscosity reduction than monovalent salts. The divalent cations present in divalent salts may suppress the viscoelastic behavior of the polymer solution at a greater amount than monovalent cations and minimize repulsive forces among the charged groups present in the polymer chain. The hydrolyzed polyacrylamide interacts strongly with divalent cations, such as $Ca^{2+}$ and $Mg^{2+}$, which results in a reduction in molecular dimensions and, consequently, viscosity. Accordingly, the coil conformation of hydrolyzed polyacrylamide (HPAM) molecules in aqueous solutions makes the molecules sensitive to the ionic environment.

Figure 1:
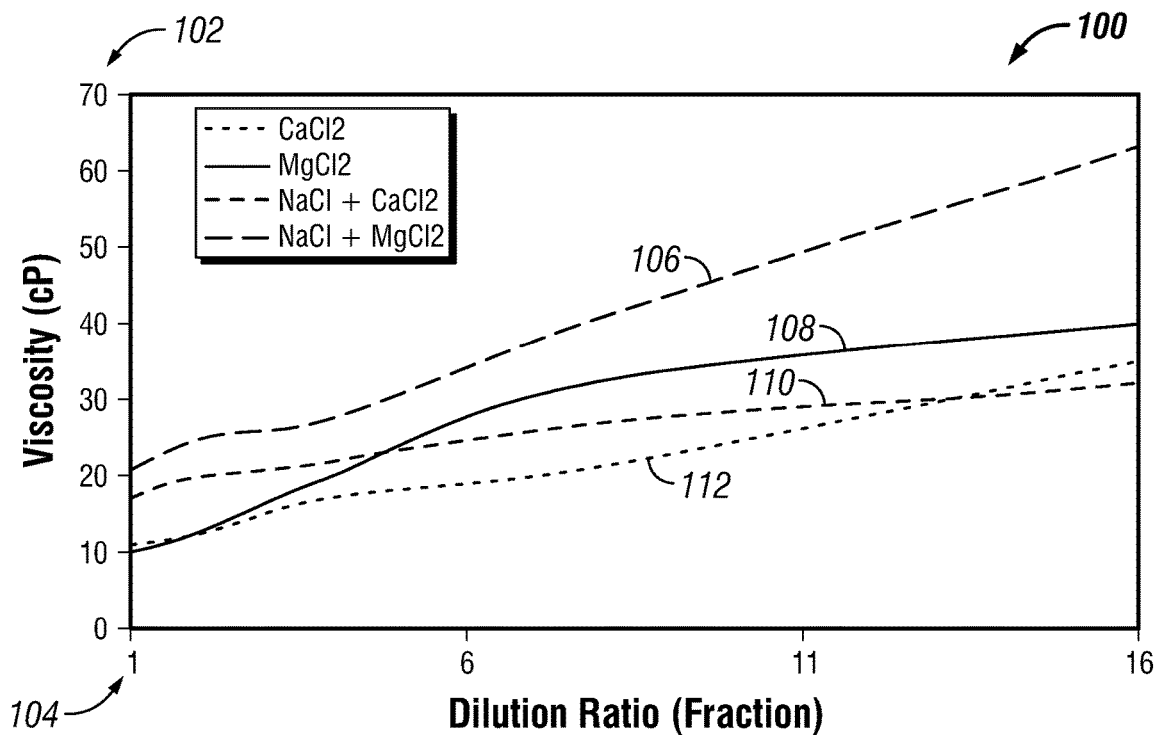
FIG. 1 is a plot depicting the viscosity of polymer solutions having divalent salts $MgCl_2$ and $CaCl_2$)) and a mixture of divalent salts and monovalent salts ($NaCl+MgCl_2$ and $NaCl+CaCl_2$)) and a 0.25 percent by weight (wt %) of a high molecular weight (for example, $12\times10^6$ Daltons) polyacrylamide at 95 degrees Celsius (° C.) in accordance with an embodiment of the disclosure.

For example, when comparing the viscosity values of divalent salts (for example, $MgCl_2$ and $CaCl_2$)) and mixtures of divalent salts in the presence of sodium chloride ($NaCl+MgCl_2$ and $NaCl+CaCl_2$)), the influence of the monovalent ions clearly shows a reduction in the repulsion effect that results in higher viscosities. FIG. 1 is a plot 100 depicting the viscosity of polymer solutions having divalent salts (for example, $MgCl_2$ and $CaCl_2$)) and a mixture of divalent salts and monovalent salts ($NaCl+MgCl_2$ and $NaCl+CaCl_2$)) for polymer solutions and having a 0.25 weight (wt) % of a high molecular weight polyacrylamide at 95° C. As shown in FIG. 1, the Y-axis 102 corresponds to the viscosity in centipoise (cP) and the X-axis 104 corresponds to the dilution ratio of the salts. As shown in FIG. 1, the $NaCl+MgCl_2$ solution depicted by line 106 has higher viscosities at all dilution ratios as compared to the $MgCl_2$ solution depicted by line 108. Similarly, the $NaCl+CaCl_2$) solution depicted by line 110 has higher viscosities at most dilution ratios less than about 14 as compared to the $NaCl+CaCl_2$) solution depicted by line 112. Thus, it is believed that the monovalent cations may replace the divalent cations at the polar sites along the polyacrylamide coils, permitting the coils to unwind and exert their viscous properties in the solution when compared to the interactions of divalent cations at the same sites.

In view of the foregoing, embodiments of the disclosure include oil recovery compositions and processes for enhancing oil recovery from a reservoir formation. The oil recovery compositions and processes described in this disclosure may enhance oil recovery from a reservoir formation at reduced cost as compared to conventional enhanced oil recovery compositions. In some embodiments, an oil recovery composition includes an oil recovery polymer and an aqueous solution having a monovalent cations to divalent cations ratio in the range of about 3:1 to about 4.5:1. In some embodiments, the hydrolyzable polymer includes polyacrylamide. In some embodiments the hydrolyzable polymer includes a partially hydrolyzed polyacrylamide (HPAM). For example, in some embodiments, a suitable HPAM may have a molecular weight of about 12 million, a degree of hydrolysis (HD) of 3.28%, and a solid content of 90.56%. In some embodiments, the polymer is CA8036 manufactured by Bomochem of China. In some embodiments, the aqueous solution includes monovalent salts and divalent salts having a ratio in the range of about 3:1 to about 4.5:1. In some embodiments, the aqueous solution is formed from a brine recovered from production water. As used in the disclosure, the term "production water" (also referred to as "produced water") refers to water produced during the recovery of hydrocarbons from a hydrocarbon reservoir formation. In some embodiments, the aqueous solution is formed from a brine of treated seawater or untreated seawater. As used herein, the term "treated seawater" refers to seawater that is treated to remove components unsuitable for use in oil recovery compositions, such as seawater that is treated to remove biofoulants, dissolved oxygen, suspended or dissolved solids, or any combination thereof. In some embodiments, the aqueous solution is formed from a brine of aquifer water. In some embodiments, the aqueous solution may be formed by adding a monovalent salt to a brine having an initial monovalent cations to divalent cations ratio such that an aqueous solution (that is, a modified brine) having a monovalent cations to divalent cations ratio in the range of about 3:1 to about 4.5:1 is formed.

In some embodiments, a brine may be recovered from produced water and analyzed to determine a ratio of monovalent cations to divalent cations. A monovalent salt may be added to the brine to modify the ratio of monovalent cations to divalent cations and achieve a target viscosity of an oil recovery composition. The target viscosity may be determined for conditions of a hydrocarbon reservoir formation. In some embodiments, the ratio of monovalent cations to divalent cations may be modified to be in the range of about 3:1 to about 4.5:1. In some embodiments, the monovalent salt is NaCl. In some embodiments the brine and monovalent salts may be mixed for a mixing time period. An hydrolyzable polymer may be added to the brine to form the oil recovery composition having the target viscosity and a monovalent cations to divalent cations ratio in the range of about 3:1 to about 4.5:1. In some embodiments, the polymer has a concentration of about 0.05% by weight to about 0.5% by weight. In some embodiments, the hydrolyzable polymer is polyacrylamide.

In some embodiments, the oil recovery composition described in the disclosure may be introduced (for example, pumped) downhole to enhance oil recovery in a hydrocarbon reservoir formation. For example, an oil recovery composition having a hydrolyzable polymer and a brine having a monovalent cations to divalent cations ratio in the range of about 3:1 to about 4.5:1 may prepared at the surface and introduced downhole to enhance oil recovery from a hydrocarbon reservoir formation.

EXAMPLES

The following examples are included to demonstrate embodiments of the disclosure. It should be appreciated by those of skill in the art that the techniques and compositions disclosed in the example which follows represents techniques and compositions discovered by the inventors to function well in the practice of the disclosure, and thus can be considered to constitute modes for its practice. However, those of skill in the art should, in light of the present disclosure, appreciate that many changes can be made in the specific embodiments which are disclosed and still obtain a like or a similar result without departing from the spirit and scope of the disclosure.

The following non-limiting examples of oil recovery compositions having various monovalent cations to divalent cations ratios were tested and compared against a solution of brine and a polyacrylamide polymer at various dilutions with water.

A first solution was formed from a brine recovered from production water and a polyacrylamide polymer. The brine included a concentration of monovalent cations of 0.9638 milliequivalents per milliliter (meq/mL) and a concentration of divalent cations of 0.4926 meq/mL, such that the monovalent cations to divalent cations ratio of the first solution was 1.96:1. The viscosity of the first solution was measured at various dilutions with water.

A second solution was formed by adding a monovalent salt NaCl, to the first solution, such that the second solution has an increased ratio of monovalent cations to divalent cations. The viscosity of the second solution was measured at different concentrations of NaCl, that is at different ratios of monovalent cations to divalent cations.

The polyacrylamide polymer used in the solutions in CA8036 partially hydrolyzed polyacrylamide (HPAM) manufactured by Bomochem of China. The polymer has a molecular weight of about $12 \times 10^6$ Daltons. The degree of hydrolysis is 3.28% and the solid content is 92.37%. The polymer was prepared in concentrations of 0.25 wt % in the first solution and 0.25 wt % in the second solution.

The dimensionless viscosity of each measured solutions was also determined, according to Equation 1:

$$\mu D = \frac{\mu x - \mu W}{\mu 6 - \mu W} \quad (1)$$

Where $\mu D$ is the dimensionless viscosity, $\mu x$ is the viscosity at X revolutions per minute (RPM) in centipoise (cP), $\mu w$ is the viscosity of water in cP (assumed to be 0.34), and $\mu 6$ is the viscosity at 6 revolutions-per-minute (RPM) in centipoise (cP).

The viscosity of each solution was measured using a Brookfield DV-II+Pro viscometer manufactured by Brookfield Engineering of Middleboro, Mass., USA, using an S-18 Spindle sample adapter. The temperature was controlled using a TC-502 Temperature Control Bath by Brookfield Engineering of Middleboro, Mass., USA. At high temperatures, a cap was attached to the measuring cup to minimize evaporation. The measurements were taken after a time period in order for the solution to reach the temperature shown in the digital controller in the viscometer.

The composition of the brine recovered from production water and used in the first and second solutions, in milligrams/liter (mg/L), is shown in Table 1:

TABLE 1

| Composition of Example Brine Recovered from Production Water | |
|---|---|
| $Na^+$ | 22166 mg/L |
| $Ca^{2+}$ | 8128 mg/L |
| $Mg^{2+}$ | 1052 mg/L |
| $K^+$ | 1021 mg/L |
| $SO_4^{2-}$ | 384 mg/L |
| $Cl^-$ | 51810 mg/L |
| $CO_3^{2-}$ | 0 mg/L |
| $HCO_3$ | 154 mg/L |
| Total Dissolved Solids (TDS) | 84175 mg/L |
| Anions | 52348 mg/L |
| Cations | 31346 mg/L |
| Monovalent Cations to Divalent Cations Ratio (mass ratio) | 2.526 |

The composition of the brine recovered from production water and used in the first and second solutions, in milliequivalents/milliliter (meq/mL), is shown in Table 2:

TABLE 2

| Composition of Example Brine Recovered from Production Water | |
|---|---|
| $Na^+$ | 0.9637 |
| $Ca^{2+}$ | 0.4064 |
| $Mg^{2+}$ | 0.0862 |
| $K^+$ | 0.0262 |
| $SO_4^{2-}$ | 0.0080 |
| $Cl^-$ | 1.4594 |
| $CO_3^{2-}$ | 0.0000 |
| $HCO_3$ | 0.0025 |
| Anions ($C_{51}$) | 1.4700 |
| Divalent Cations ($C_{61}$) | 0.4926 |
| Monovalent Cations to Divalent Cations Ratio (meq/ml) | 2.01 |

The composition of the second solution at different concentrations of NaCl is shown in Table 3:

TABLE 3

Composition of Example Brine and Polymer Solution at Different NaCl Concentrations

| | 2,500 mg/L NaCl | 5,000 mg/L NaCl | 10,000 mg/L NaCl | 15,000 mg/L NaCl | 21,300 mg/L NaCl |
|---|---|---|---|---|---|
| $Na^+$ (mg/L) | 23149 | 24133 | 26100 | 28067 | 30624 |
| $Ca^{2+}$ (mg/L) | 8128 | 8128 | 8128 | 8128 | 8128 |
| $Mg^{2+}$ (mg/L) | 1052 | 1052 | 1052 | 1052 | 1052 |
| $K^+$ (mg/L) | 1021 | 1021 | 1021 | 1021 | 1021 |
| $SO_4^{2-}$ (mg/L) | 384 | 384 | 384 | 384 | 384 |
| $Cl^-$ (mg/L) | 53327 | 54843 | 57876 | 60909 | 64852 |
| $CO_3^{2-}$ (mg/L) | 0 | 0 | 0 | 0 | 0 |
| $HCO_3$ (mg/L) | 154 | 154 | 154 | 154 | 154 |
| Anions ($C_{51}$) (meq/ml) | 1.513 | 1.555 | 1.641 | 1.726 | 1.834 |
| Divalent Cations ($C_{61}$) (meq/ml) | 0.493 | 0.493 | 0.493 | 0.493 | 0.493 |
| Monovalent Cations to Divalent Cations Ratio (based on meq/ml) | 2.096 | 2.183 | 2.356 | 2.530 | 2.749 |
| Monovalent Cations to Divalent Cations Ratio (mass ratio) | 2.633 | 2.740 | 2.954 | 3.168 | 3.438 |

The viscosity of the first solution of production water brine and 0.25 wt % polymer concentration was measured at various brine dilutions at 95° C. The viscosity of the second solution of production water brine, 0.25 wt % polymer concentration, and added NaCl was measured at different NaCl concentrations at 95° C. Additionally, the dimensionless viscosity for the solutions was determined from the measured viscosity. The viscosity and dimensionless viscosity at various speeds for the first solution, and the second solution having concentrations of NaCl, are shown in Table 4:

TABLE 4

Viscosity and Dimensionless Viscosity of Example Brine and Polymer Solution at Different NaCl Concentrations

| NaCl Concentration (mg/L) | Viscosity μ (cP) | Speed ω (RPM) | Dimensionless viscosity $μ_D$ (unitless) |
|---|---|---|---|
| Brine (no added NaCl) | 10.5 | 6 | 1.0 |
| | 8.5 | 12 | 0.8 |
| | 6.5 | 30 | 0.6 |
| | 5.5 | 60 | 0.5 |
| 2,500 | 9.0 | 6 | 1.0 |
| | 6.0 | 12 | 0.7 |
| | 5.1 | 30 | 0.5 |
| | 4.5 | 60 | 0.5 |
| 5,000 | 14.5 | 6 | 1.0 |
| | 7.8 | 12 | 0.5 |
| | 6.8 | 30 | 0.5 |
| | 5.0 | 60 | 0.3 |
| 10,000 | 18 | 6 | 1.0 |
| | 9.5 | 12 | 0.5 |
| | 7.1 | 30 | 0.4 |
| | 5.8 | 60 | 0.3 |
| 15,000 | 19.5 | 6 | 1.0 |
| | 10.5 | 12 | 0.5 |
| | 7.5 | 30 | 0.4 |
| | 5.9 | 60 | 0.3 |
| 21,300 | 12.5 | 6 | 1.0 |
| | 7.5 | 12 | 0.6 |
| | 5.8 | 30 | 0.4 |
| | 4.8 | 60 | 0.4 |

Figure 2:
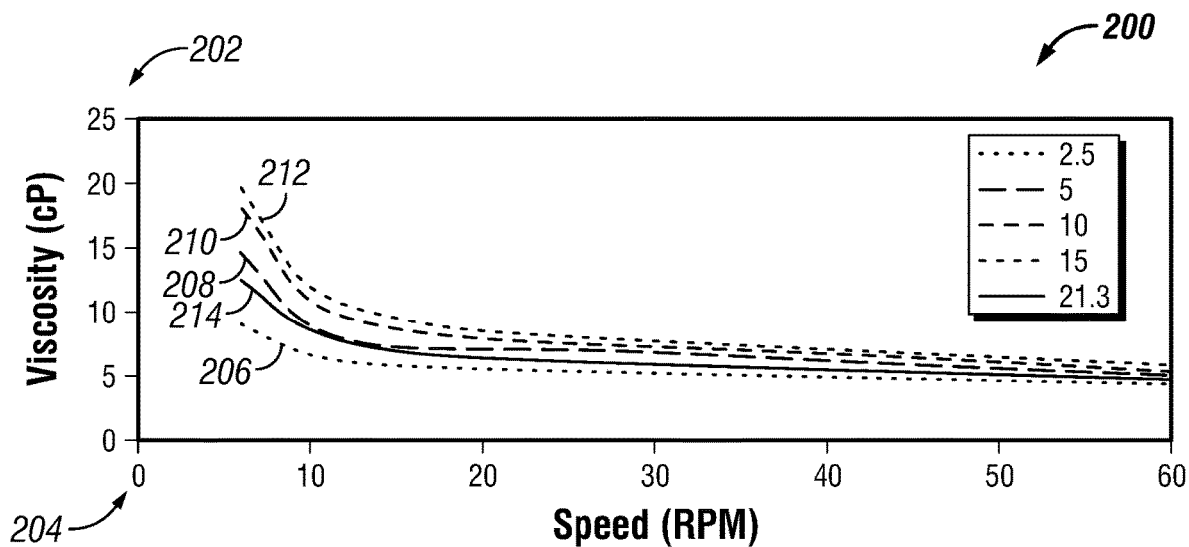
FIG. 2 is a plot of the viscosity vs. rotational speed for a solution of production water brine, 0.25 wt % polymer, and various NaCl concentrations in accordance with an embodiment of the disclosure.

FIG. 2 is a plot 200 of the measured viscosity vs. speed for the second solution of production water brine, 0.25 wt % polymer and different NaCl concentrations (that is, at different ratios of monovalent cations to divalent cations achieved by the addition of NaCl). As shown in FIG. 2, the Y-axis 202 corresponds to the viscosity in centipoise (cP) and the X-axis 204 corresponds to the speed of the viscometer in RPM. The viscosities at the different concentrations of NaCl in the second solution are depicted as different lines in the plot 200. For example, the viscosities of the second solution at 2,500 mg/L NaCl are shown by line 206, the viscosities of the second solution at 5,000 mg/L NaCl are shown by line 208, the viscosities of the second solution at 10,000 mg/L are shown by line 210, the viscosities of the second solution at 15,000 mg/L NaCl are shown by line 212, and the viscosities of the second solution at 21,300 mg/L NaCl are shown by line 214. As shown in the plot 200 and as mentioned supra, at higher concentrations such as 21,300 mg/L, the viscosity of the second solution no longer increases as compared to lower concentrations.

As shown in Table 4 and FIG. 2, the addition of a monovalent salt, NaCl, to the brine having both monovalent salts and divalent salts may increase the viscosity of the solution as greater concentrations of NaCl and, consequently, increased ratios of monovalent cations to divalent cations are reached. At certain higher concentrations of monovalent salt, such as 21,300 mg/L, the viscosity of the brine and polymer solution ceases to increase. As shown in Table 4, the increased NaCl concentrations increase the ratio of monovalent cations (such as $Na^+$) in the second solution to divalent cations (such as $Ca^{2+}$ and $Mg^{2+}$). As discussed supra, a higher viscosity reduction may occur in the presence of divalent cations. Thus, at these higher ratios of monovalent cations to divalent cations, the viscosity reduction effect of the divalent cations discussed supra may be mitigated by the increased ratio of monovalent cations to divalent cations.

As also shown in Tables 4 and 5, the viscosity of the second solution at certain NaCl concentrations is greater than the viscosity of the first solution at certain brine dilutions. As will be appreciated, the viscosity increases at lower speeds may be particularly applicable in downhole applications in a reservoir formation. Thus, a target viscosity for an oil recovery composition may be achieved by adding a monovalent salt to a desired monovalent cations to divalent cations ratio and without the addition of further polymer or water treatment. An oil recovery composition at the target viscosity may have improved resistance to high salinity or hardness and may be relatively less expensive as compared to other approaches used to achieve a target viscosity, such as dilution, water softening, higher polymer concentrations, more resistant polymers, or combinations of these approaches.

Accordingly, the use of the oil recovery composition described in the disclosure may reduce the consumption of polymer and provide for the use of less resistant and less expensive polymer, thus lowering operational costs associated with the use of polymer oil recovery compositions. Additionally, use of the oil recovery composition described in the disclosure may eliminate the use of water treatment (for example, water softening facilities) and further decrease the operational costs of enhanced oil recovery operations.

Oil Recovery Compositions

In some embodiments, an oil recovery composition may include a hydrolyzable polymer and monovalent cations to divalent cations ratio in the range of about 2.5:1 to about 3:1. In some embodiments, an oil recovery composition may include a brine, a hydrolyzable polymer, and a monovalent cations to divalent cations ratio in the range of about 2.5:1 to about 3:1. In some embodiments, the brine may be recovered from production water. As used herein, the term "brine" may include synthetic seawater. In such embodiments, a monovalent cations to divalent cations ratio in the range of about 2.5:1 to about 3:1 may be achieved by adding a monovalent salt to the brine recovered from production water to form a modified brine having a modified monovalent cations to divalent cations ratio. In some embodiments, the brine is sourced from treated seawater or untreated seawater. In some embodiments, the brine is sourced from aquifer water. In some embodiments, an oil recovery composition may include a brine recovered from production water, polyacrylamide, and a monovalent cations to divalent cations ratio in a range of about 2.5:1 to about 3:1. In some embodiments, an oil recovery composition may have a composition expressed as a ratio of monovalent salts to divalent salts.

In some embodiments, the polymer may have a concentration of about 0.05 wt % to about 0.5 wt %. For example, in some embodiments, the hydrolyzable polymer may have a concentration of about 0.25 wt %. In some embodiments, the oil recovery composition may include a surfactant.

It should be appreciated that embodiments of the enhanced oil recovery composition (EOR) having a monovalent cations to divalent cations ratio in the range of about 3:1 to about 4.5:1 may include any suitable monovalent salts and divalent. In some embodiments, the monovalent salt may include NaCl. Other embodiments may include other monovalent salts or divalent salts.

In some embodiments, the polymer of the oil recovery composition may have a maximum molecular weight that ensures the polymer retains the ability to penetrate through a porous medium in a reservoir for which the oil recovery composition will be used. In some embodiments, the hydrolyzable polymer may include polyacrylamides, such as partially hydrolyzed polyacrylamides (HPAMs). In some embodiments, the polymer may include a polyacrylamide having a molecular weight of $12 \times 10^6$ Daltons. For example, in some embodiments, a suitable HPAM may have a molecular weight of about 12 million, a degree of hydrolysis (HD) of 3.28%, and a solid content of 90.56%. In some embodiments, the polymer is CA8036 HPAM manufactured by Bomochem of China. In some embodiments, the hydrolyzable polymer may include ionic polymers (for example, polymers having ions across the polymer chain) suitable for oil recovery applications.

Figure 3:
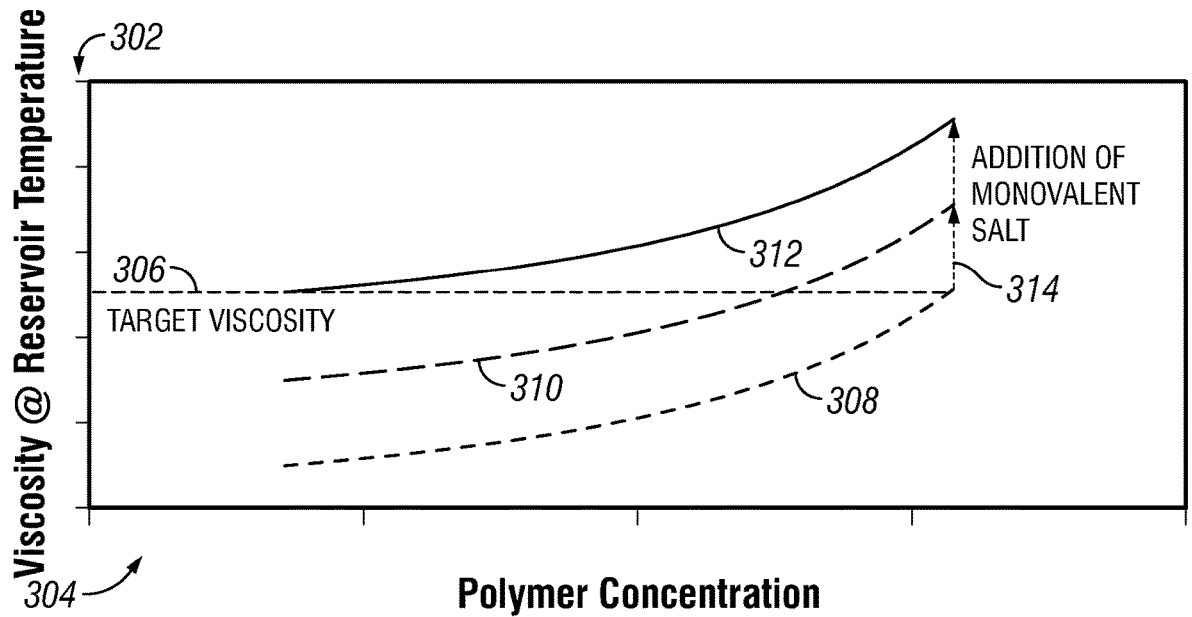
FIG. 3 is a plot of the viscosity of a hypothetical oil recovery composition having various polymer concentrations and the addition of a monovalent salt in accordance with an embodiment of the disclosure.

In some embodiments, a target viscosity of an oil recovery composition may be achieved by the addition of a monovalent salt, such as NaCl, to a brine and polymer solution, such as an existing oil recovery composition. FIG. 3 is a plot 300 depicting the viscosity of a hypothetical oil recovery composition having various polymer concentrations in accordance with an embodiment of the disclosure. As shown in FIG. 3, the y-axis 302 corresponds to a viscosity at a reservoir temperature and the x-axis 304 corresponds to polymer concentrations of the oil recovery compositions. The target viscosity is illustrated by line 306. The lines 308, 310, and 312 illustrate the viscosity of an oil recovery composition at various polymer concentrations and monovalent salt concentrations (that is, at various ratios of monovalent cations to divalent cations).

As further shown in FIG. 3, the addition of a monovalent salt, as illustrated by arrow 314, may increase the viscosity of an oil recovery composition to the target viscosity without requiring an increase in polymer concentration. For example, as shown by lines 308, 310, and 312 the target viscosity may be achieved by the addition of a monovalent salt line at a lower polymer concentration than at higher polymer concentration and lower monovalent salt concentration, as shown by line 310 compared to line 308 and line 312 compared to line 310.

Figure 4:
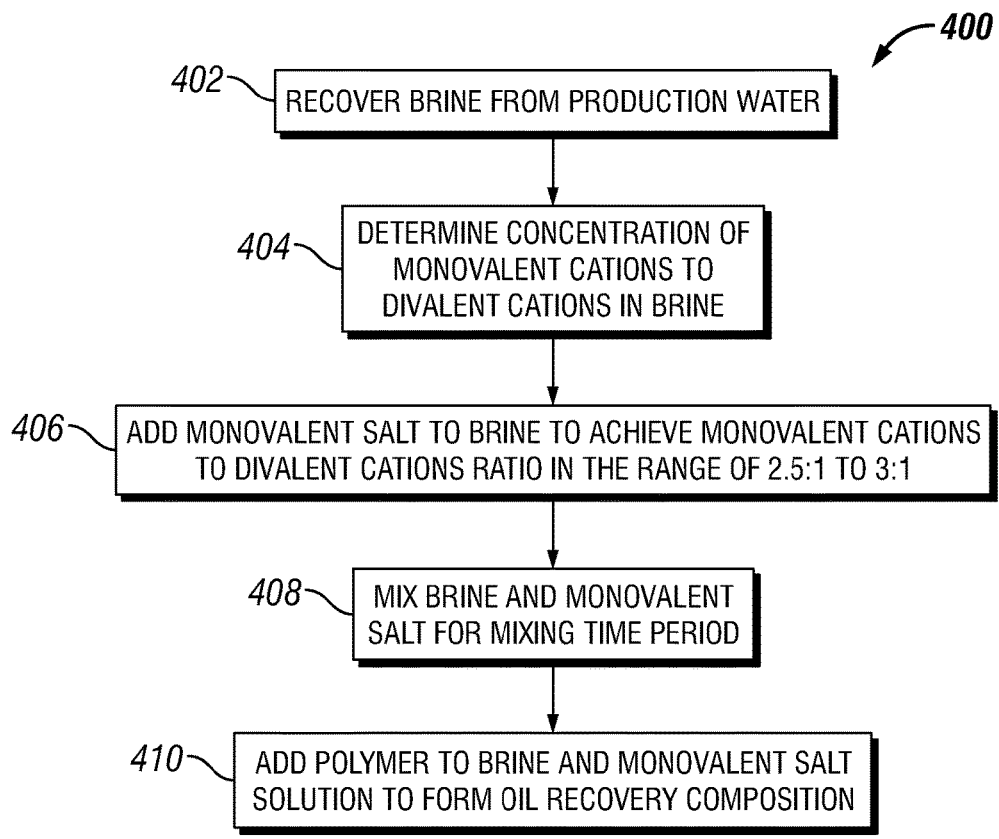
FIG. 4 is a flowchart of a process for forming an enhanced oil recovery composition from a brine recovered from produced water and having a monovalent cations to divalent cations ratio in the range of 3:1 to 4.5:1.

As mentioned supra, in some embodiments an enhanced oil recovery composition may be formed from produced water. FIG. 4 depicts a process 400 for forming an enhanced oil recovery composition from a brine recovered from produced water by modifying the monovalent cations to divalent cations ratio of the brine to achieve a target viscosity of the composition. It should be appreciated that the process 400 may be similarly applied to brines obtained from other sources, such as treated seawater, untreated seawater, aquifer water, etc. Initially, a brine may be recovered from production water (block 400). The concentration of monovalent ions and divalent ions in the brine may be determined (block 402), such as by determining the composition of the brine. Next, a monovalent salt may be added to the brine to modify the ratio of monovalent cations to divalent cations to a range of about 3:1 to about 4.5:1 (block 404). For example, an amount of a monovalent salt such as NaCl may be added to the brine to form a modified brine, and the composition of the modified brine may be determined to evaluate the monovalent cations to divalent cations ratio. The brine and monovalent salts may be mixed for a mixing time period (block 406) to ensure the elimination of salt precipitation and evaluate possible compatibility issues that may affect suitability of the brine for injection.

Next, a polymer may be added to the brine and monovalent salt solution to form the enhanced oil recovery composition having a monovalent cations to divalent cations ratio in a range of about 3:1 to about 4.5:1 and having the target viscosity (block 408). The target viscosity may be determined for conditions of the hydrocarbon reservoir formation. The concentration of monovalent salt (or, in some embodiments, divalent salt) added to achieve a target viscosity may depend on the selected polymer, the reservoir temperature, and the salinity of the brine. In some embodiments, the long term heat degradation in the reservoir and the shear degradation at constructions at the surface may also be considerations in achieving the target viscosity. In some embodiments, an achievable target viscosity may be limited by the injectivity of a well (that is, the reservoir characteristics and the associated injection volumes). In some embodiments, a surfactant may be added to form the enhanced oil recovery composition.

In some embodiments, the oil recovery an oil recovery composition having a monovalent cations to divalent cations ratio in the range of about 3:1 to about 4.5:1 may be used to enhance oil recovery from a hydrocarbon reservoir formation. The oil recovery composition may be prepared on the surface by adding a monovalent salt to a brine, such as a brine recovered from production water or from other sources (for example, treated seawater, untreated seawater, or aquifer water). For example, in some embodiments, an oil recovery composition having a brine and a hydrolyzable polymer, and having a monovalent cations to divalent cations ratio in the range of about 2.5:1 to about 3:1 may be prepared on the surface. In some embodiments, an oil recovery composition prepared on the surface may be prepared to achieve a target viscosity. As discussed supra, preparation of the oil recovery composition may be performed without the addition of water to the brine for dilation, without water treatment facilities, and without relatively high concentrations of polymer. For example, a target viscosity of an oil recovery composition having a hydrolyzable polymer may be achieved solely by the addition of a monovalent salt without other additives until a desired target viscosity (and corresponding monovalent cations to divalent cations ratio) is reached. The oil recovery composition may be introduced downhole (for example, injected or pumped) into the reservoir formation. In some embodiments, additional oil recovery compositions or water may be subsequently introduced downhole. Displaced oil may then be recovered from the reservoir formation.

Ranges may be expressed in the disclosure as from about one particular value, to about another particular value, or both. When such a range is expressed, it is to be understood that another embodiment is from the one particular value, to the other particular value, or both, along with all combinations within said range.

Throughout this application, where patents or publications are referenced, the disclosures of these references in their entireties are intended to be incorporated by reference into this application, in order to more fully describe the state of the art to which the disclosure pertains, except when these references contradict the statements made in the disclosure.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Changes may be made in the elements described in the disclosure without departing from the spirit and scope of the disclosure as described in the following claims. Headings used in the disclosure are for organizational purposes only and are not meant to be used to limit the scope of the description.

What is claimed is:

1. A method of enhancing oil recovery in a hydrocarbon reservoir formation, comprising:

adding a monovalent salt to a brine to modify a mass ratio of monovalent cations to divalent cations of the brine, thereby forming a modified brine having a modified monovalent cations to divalent cations mass ratio in a range of range of 2.5:1 to 3:1, the modified brine having a $Na^+$ concentration in the range of 22,166 milligrams/liter (mg/L) to 30.624 mg/L;

introducing an oil recovery composition into the reservoir formation, the oil recovery composition comprising:

the modified brine having the modified monovalent cations to divalent cations mass ratio, the modified monovalent cations to divalent cations mass ratio selected to achieve a target viscosity of the oil recovery composition; and polyacrylamide having a concentration of 0.05 weight (wt) % to 0.5 wt %.

2. The method of claim 1, wherein the monovalent cations comprise sodium cations.

3. The method of claim 1, wherein the divalent cations comprise at least one of calcium cations and magnesium cations.

4. The method of claim 1, wherein the target viscosity comprises at least 4 centipoise at the conditions of the hydrocarbon reservoir formation.

5. The method of claim 1, comprising preparing the oil recovery composition before introducing the oil recovery composition into the reservoir formation, the preparing comprising:

recovering the brine from production water;

adding the monovalent salt to the brine to form the modified brine; and adding the hydrolyzable polymer to the brine.

6. The method of claim 1, wherein the brine comprises treated seawater or untreated seawater.

7. The method of claim 1, wherein the brine comprises aquifer water.

8. The method of claim 1, wherein the oil recovery composition comprises a surfactant.

* * * * *